(12) United States Patent
van der Weide

(10) Patent No.: US 10,342,614 B2
(45) Date of Patent: *Jul. 9, 2019

(54) TRIAXIAL ANTENNA FOR MICROWAVE TISSUE ABLATION

(75) Inventor: Daniel W. van der Weide, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 393 days.

This patent is subject to a terminal disclaimer.

(21) Appl. No.: 13/563,050

(22) Filed: Jul. 31, 2012

(65) Prior Publication Data

US 2012/0316551 A1 Dec. 13, 2012

Related U.S. Application Data

(63) Continuation of application No. 11/452,637, filed on Jun. 14, 2006, now abandoned, which is a continuation-in-part of application No. 10/834,802, filed on Apr. 29, 2004, now Pat. No. 7,101,369.

(51) Int. Cl.
*A61B 18/18* (2006.01)
*A61B 18/00* (2006.01)

(52) U.S. Cl.
CPC .......... *A61B 18/18* (2013.01); *A61B 18/1815* (2013.01); *A61B 2018/00023* (2013.01)

(58) Field of Classification Search
CPC ............... A61B 18/18; A61B 18/1815; A61B 2018/00023
USPC ..................................... 606/32–33
See application file for complete search history.

(56) References Cited

U.S. PATENT DOCUMENTS

| | | |
|---|---|---|
| 1,542,607 A | 6/1925 | Bussmann |
| 3,800,552 A | 4/1974 | Sollami et al. |
| 3,838,242 A | 9/1974 | Goucher |
| 3,991,770 A | 11/1976 | Le Veen |
| 4,057,064 A | 11/1977 | Morrison, Jr. et al. |
| 4,074,718 A | 2/1978 | Morrison, Jr. |
| 4,312,364 A | 1/1982 | Convert et al. |
| 4,375,220 A | 3/1983 | Matvias |
| 4,446,874 A | 5/1984 | Vaguine |
| 4,494,539 A | 1/1985 | Zenitani et al. |
| 4,534,347 A | 8/1985 | Taylor |
| 4,534,547 A | 8/1985 | Cox |
| 4,557,272 A | 12/1985 | Carr |
| 4,589,424 A | 5/1986 | Vaguine |
| 4,621,642 A | 11/1986 | Chen |

(Continued)

FOREIGN PATENT DOCUMENTS

| | | |
|---|---|---|
| EP | 1186274 | 3/2002 |
| EP | 1 395 190 | 3/2004 |

(Continued)

OTHER PUBLICATIONS

Golio, "The RF and microwave handbook" Edition 2. Published, by CRC Press. 2001 ISBN 0849338592X, 97808493859626.

(Continued)

*Primary Examiner* — Michael F Peffley
*Assistant Examiner* — Samantha M Good
(74) *Attorney, Agent, or Firm* — Boyle Fredrickson, S.C.

(57) ABSTRACT

An improved antenna for microwave ablation uses a triaxial design which reduces reflected energy allowing higher power ablation and/or a smaller diameter feeder line to the antenna.

30 Claims, 2 Drawing Sheets

(56) References Cited

U.S. PATENT DOCUMENTS

| | | |
|---|---|---|
| 4,627,435 A | 12/1986 | Hoskin |
| 4,643,186 A | 2/1987 | Rosen et al. |
| 4,662,383 A | 5/1987 | Sogawa et al. |
| 4,700,716 A | 10/1987 | Kasevich et al. |
| 4,712,559 A | 12/1987 | Turner |
| 4,776,086 A | 10/1988 | Kasevich et al. |
| 4,790,311 A | 12/1988 | Ruiz |
| 4,901,719 A | 2/1990 | Trenconsky et al. |
| 4,945,912 A | 8/1990 | Langberg |
| 5,026,959 A | 6/1991 | Ito et al. |
| 5,057,104 A | 10/1991 | Chess |
| 5,057,106 A | 10/1991 | Kasevich et al. |
| 5,074,861 A | 12/1991 | Schneider et al. |
| RE33,791 E | 1/1992 | Carr |
| 5,098,429 A | 3/1992 | Sterzer |
| 5,129,396 A | 7/1992 | Rosen et al. |
| 5,150,717 A | 9/1992 | Rosen et al. |
| 5,167,619 A | 12/1992 | Wuchinich |
| 5,211,625 A | 5/1993 | Sakurai et al. |
| 5,248,312 A | 9/1993 | Langberg |
| 5,275,597 A | 1/1994 | Higgins et al. |
| 5,277,201 A | 1/1994 | Stern |
| 5,281,213 A | 1/1994 | Milder et al. |
| 5,281,217 A | 1/1994 | Edwards et al. |
| 5,295,955 A | 3/1994 | Rosen et al. |
| 5,300,099 A | 4/1994 | Rudie |
| 5,301,687 A | 4/1994 | Wong et al. |
| 5,344,418 A | 9/1994 | Ghaffari |
| 5,344,435 A | 9/1994 | Turner et al. |
| 5,348,554 A | 9/1994 | Imran et al. |
| 5,358,515 A | 10/1994 | Hurter et al. |
| 5,364,392 A | 11/1994 | Warner et al. |
| 5,366,490 A | 11/1994 | Edwards et al. |
| 5,369,251 A | 11/1994 | King et al. |
| 5,370,678 A | 12/1994 | Edwards et al. |
| 5,405,346 A | 4/1995 | Grundy et al. |
| 5,431,649 A | 7/1995 | Mulier et al. |
| 5,433,740 A | 7/1995 | Yamaguchi |
| 5,456,684 A | 10/1995 | Schmidt et al. |
| 5,462,556 A | 10/1995 | Powers |
| 5,472,423 A | 12/1995 | Gronauer |
| 5,480,417 A | 1/1996 | Hascoet et al. |
| 5,507,743 A | 4/1996 | Edwards et al. |
| 5,531,677 A | 7/1996 | Lundquist et al. |
| 5,575,794 A | 11/1996 | Walus et al. |
| 5,578,029 A | 11/1996 | Trelles et al. |
| 5,591,227 A | 1/1997 | Dinh et al. |
| 5,599,295 A | 2/1997 | Rosen et al. |
| 5,599,352 A | 2/1997 | Dinh et al. |
| 5,603,697 A | 2/1997 | Grundy et al. |
| 5,620,479 A | 4/1997 | Diederich |
| 5,647,871 A | 7/1997 | Levine et al. |
| 5,693,082 A | 12/1997 | Warner et al. |
| 5,716,389 A | 2/1998 | Walinsky |
| 5,737,384 A | 4/1998 | Fenn |
| 5,741,249 A | 4/1998 | Moss et al. |
| 5,755,752 A | 5/1998 | Segal |
| 5,755,754 A | 5/1998 | Rudie et al. |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough et al. |
| 5,788,692 A | 8/1998 | Campbell et al. |
| 5,788,694 A | 8/1998 | Vancaillie |
| 5,800,494 A | 9/1998 | Campbell et al. |
| 5,810,803 A | 9/1998 | Moss et al. |
| 5,810,804 A | 9/1998 | Gough et al. |
| 5,849,029 A | 12/1998 | Eckhouse et al. |
| 5,902,251 A | 5/1999 | vanHooydonk |
| 5,921,935 A | 7/1999 | Hickey |
| 5,957,969 A | 9/1999 | Warner et al. |
| 5,963,082 A | 10/1999 | Dick et al. |
| 5,995,875 A | 11/1999 | Blewett et al. |
| 6,002,968 A | 12/1999 | Edwards |
| 6,002,986 A | 12/1999 | Mito |
| 6,012,457 A | 1/2000 | Lesh |
| 6,016,811 A | 1/2000 | Knopp et al. |
| 6,026,331 A | 2/2000 | Feldberg et al. |
| 6,044,846 A | 4/2000 | Edwards |
| 6,056,744 A | 5/2000 | Edwards |
| 6,067,475 A | 5/2000 | Graves et al. |
| 6,073,052 A | 6/2000 | Zelickson et al. |
| 6,083,255 A | 7/2000 | Laufer et al. |
| 6,097,985 A | 8/2000 | Kasevich et al. |
| 6,102,885 A | 8/2000 | Bass |
| 6,104,959 A | 8/2000 | Spertell |
| 6,106,524 A | 8/2000 | Eggers et al. |
| 6,188,930 B1 | 2/2001 | Carson |
| 6,190,382 B1 | 2/2001 | Ormsby et al. |
| 6,208,903 B1 | 3/2001 | Richards et al. |
| 6,223,085 B1 | 4/2001 | Dann et al. |
| 6,230,060 B1 | 5/2001 | Mawhinney |
| 6,235,022 B1 | 5/2001 | Hallock et al. |
| 6,245,062 B1 | 6/2001 | Berube et al. |
| 6,251,128 B1 | 6/2001 | Knopp et al. |
| 6,254,598 B1 | 7/2001 | Edwards et al. |
| 6,273,384 B1 | 8/2001 | Altshuler et al. |
| 6,273,885 B1 | 8/2001 | Kopp et al. |
| 6,277,113 B1 | 8/2001 | Berube |
| 6,287,302 B1 | 9/2001 | Berube |
| 6,306,130 B1 | 10/2001 | Anderson et al. |
| 6,306,132 B1 | 10/2001 | Moorman et al. |
| 6,312,427 B1 | 11/2001 | Berube et al. |
| 6,325,796 B1 * | 12/2001 | Berube et al. .................. 606/33 |
| 6,347,251 B1 | 2/2002 | Deng |
| 6,355,033 B1 | 3/2002 | Moorman et al. |
| 6,364,876 B1 | 4/2002 | Erb et al. |
| 6,383,182 B1 | 5/2002 | Berube et al. |
| 6,398,781 B1 | 6/2002 | Goble et al. |
| 6,409,724 B1 * | 6/2002 | Penny et al. .................... 606/41 |
| 6,427,089 B1 | 7/2002 | Knowlton |
| 6,471,696 B1 | 10/2002 | Berube et al. |
| 6,500,174 B1 | 12/2002 | Maguire et al. |
| 6,506,189 B1 | 1/2003 | Rittman, III et al. |
| 6,514,249 B1 | 2/2003 | Maguire et al. |
| 6,524,308 B1 | 2/2003 | Muller et al. |
| 6,527,768 B2 | 3/2003 | Berube |
| 6,546,077 B2 | 4/2003 | Chornenky et al. |
| 6,575,969 B1 | 6/2003 | Rittman, III et al. |
| 6,577,903 B1 | 6/2003 | Cronin et al. |
| 6,582,426 B2 | 6/2003 | Moorman et al. |
| 6,585,733 B2 | 7/2003 | Wellman |
| 6,622,731 B2 | 9/2003 | Daniel et al. |
| 6,635,055 B1 | 10/2003 | Cronin |
| 6,652,520 B2 | 11/2003 | Moorman et al. |
| 6,663,625 B1 | 12/2003 | Ormsby et al. |
| 6,668,197 B1 | 12/2003 | Habib et al. |
| 6,673,068 B1 | 1/2004 | Berube |
| 6,683,625 B2 | 1/2004 | Muthusamy et al. |
| 6,740,107 B2 | 5/2004 | Loeb et al. |
| 6,749,606 B2 | 6/2004 | Keast et al. |
| 6,752,767 B2 | 6/2004 | Turovskiy et al. |
| D493,531 S | 7/2004 | Padain |
| 6,770,070 B1 | 8/2004 | Balbierz |
| 6,780,178 B2 | 8/2004 | Palanker et al. |
| 6,786,904 B2 | 9/2004 | Doscher et al. |
| 6,802,840 B2 | 10/2004 | Chin et al. |
| 6,817,999 B2 | 11/2004 | Berube et al. |
| 6,823,218 B2 | 11/2004 | Berube |
| 6,847,848 B2 | 1/2005 | Sterzer et al. |
| 6,849,075 B2 | 2/2005 | Bertolero et al. |
| 6,852,091 B2 | 2/2005 | Edwards et al. |
| 6,866,624 B2 | 3/2005 | Chornenky et al. |
| 6,866,663 B2 | 3/2005 | Edwards et al. |
| 6,878,147 B2 | 3/2005 | Maguire et al. |
| 6,893,436 B2 | 5/2005 | Woodard et al. |
| 6,893,536 B2 | 5/2005 | Ilmonen et al. |
| 6,898,454 B2 | 5/2005 | Atalar et al. |
| D507,649 S | 7/2005 | Padain |
| 6,918,905 B2 | 7/2005 | Neuberger |
| 6,957,108 B2 | 10/2005 | Turner et al. |
| 6,962,586 B2 | 11/2005 | Berube et al. |
| 6,972,016 B2 | 12/2005 | Hill, III et al. |
| 6,976,986 B2 | 12/2005 | Berube |

(56) References Cited

U.S. PATENT DOCUMENTS

| | | |
|---|---|---|
| 7,022,105 B1 | 4/2006 | Edwards |
| 7,033,352 B1 | 4/2006 | Gauthier et al. |
| 7,101,369 B2 | 9/2006 | van der Welde |
| 7,115,126 B2 | 10/2006 | Berube et al. |
| 7,147,632 B2 | 12/2006 | Prakash et al. |
| 7,153,298 B1 | 12/2006 | Cohen |
| 7,156,842 B2 | 1/2007 | Sartor et al. |
| 7,160,289 B2 | 1/2007 | Cohen |
| 7,160,292 B2 | 1/2007 | Moorman et al. |
| 7,184,824 B2 | 2/2007 | Hashimshony |
| 7,197,363 B2 | 3/2007 | Prakash et al. |
| 7,266,407 B2 | 9/2007 | Li et al. |
| 7,311,703 B2 | 12/2007 | Turovskiy et al. |
| 7,318,824 B2 | 1/2008 | Prakash et al. |
| 7,331,960 B2 | 2/2008 | Schaer |
| 7,381,208 B2 | 6/2008 | van der Walt et al. |
| 7,400,929 B2 | 7/2008 | Zelickson et al. |
| 7,467,015 B2 | 12/2008 | van der Weide |
| 7,601,149 B2 | 10/2009 | DiCarlo et al. |
| 7,722,620 B2 | 5/2010 | Truckai et al. |
| 7,826,904 B2 | 11/2010 | Appling et al. |
| 2002/0022836 A1 | 2/2002 | Goble et al. |
| 2002/0040185 A1 | 4/2002 | Atalar et al. |
| 2002/0087151 A1 | 7/2002 | Mody et al. |
| 2002/0087156 A1 | 7/2002 | Maguire et al. |
| 2002/0103486 A1* | 8/2002 | Cucin ............. A61B 17/32002 606/49 |
| 2002/0111619 A1 | 8/2002 | Keast et al. |
| 2002/0133148 A1 | 9/2002 | Daniel et al. |
| 2002/0165532 A1 | 11/2002 | Hill, III et al. |
| 2002/0173780 A1 | 11/2002 | Altshuler et al. |
| 2002/0193786 A1 | 12/2002 | Berube et al. |
| 2003/0024538 A1 | 2/2003 | Edwards et al. |
| 2003/0060813 A1 | 3/2003 | Loeb et al. |
| 2003/0065317 A1 | 4/2003 | Rudie et al. |
| 2003/0065319 A1 | 4/2003 | Wellman |
| 2003/0088242 A1 | 5/2003 | Prakash et al. |
| 2003/0109862 A1* | 6/2003 | Prakash et al. ............. 606/33 |
| 2003/0195499 A1 | 10/2003 | Prakash et al. |
| 2003/0208200 A1 | 11/2003 | Palanker et al. |
| 2004/0082859 A1 | 4/2004 | Schaer |
| 2004/0133254 A1 | 7/2004 | Sterzer et al. |
| 2004/0243200 A1 | 12/2004 | Turner et al. |
| 2005/0011885 A1 | 1/2005 | Seghatol et al. |
| 2005/0015081 A1 | 1/2005 | Turovskiy et al. |
| 2005/0062666 A1 | 3/2005 | Prakash et al. |
| 2005/0065512 A1 | 3/2005 | Schaer |
| 2005/0075629 A1 | 4/2005 | Chapelon et al. |
| 2005/0084490 A1 | 4/2005 | Adams et al. |
| 2005/0085881 A1 | 4/2005 | Prakash et al. |
| 2005/0107692 A1 | 5/2005 | Li et al. |
| 2005/0107870 A1 | 5/2005 | Wang et al. |
| 2005/0143726 A1 | 6/2005 | Bortkiewicz |
| 2005/0149010 A1 | 7/2005 | Turovskiy et al. |
| 2005/0165389 A1 | 7/2005 | Swain et al. |
| 2005/0177148 A1 | 8/2005 | van der Walt et al. |
| 2005/0245919 A1 | 11/2005 | van der Welde |
| 2005/0246920 A1 | 11/2005 | Vitullo et al. |
| 2006/0155270 A1 | 7/2006 | Hancock et al. |
| 2006/0264921 A1 | 11/2006 | Deutsch et al. |
| 2008/0033424 A1 | 2/2008 | van der Weide et al. |

FOREIGN PATENT DOCUMENTS

| | | |
|---|---|---|
| EP | 1 450 710 | 9/2004 |
| EP | 1499251 | 1/2005 |
| EP | 1 542 607 | 6/2005 |
| EP | 1 723 922 | 11/2006 |
| GB | 2 388 039 | 5/2003 |
| GB | 2 406521 | 6/2005 |
| WO | WO 92/04934 | 4/1992 |
| WO | WO 93/09845 | 5/1993 |
| WO | WO 97/48449 | 12/1997 |
| WO | WO 99/56643 | 11/1999 |
| WO | WO 03/039385 | 5/2003 |
| WO | WO 03/088806 | 10/2003 |
| WO | WO 03/088858 | 10/2003 |
| WO | WO 2004/004586 | 1/2004 |
| WO | WO/ 2004/033039 | 4/2004 |
| WO | WO 2004/112628 | 12/2004 |
| WO | WO 2005/034783 | 4/2005 |
| WO | WO 2006/002943 | 1/2006 |
| WO | WO 2006/005579 | 1/2006 |
| WO | WO 2006/008481 | 1/2006 |

OTHER PUBLICATIONS

Head, Hayden W., et al., "Thermal Ablation for Hepatocellular Carcinoma," Gastroenterology, 2004:127:S167-@178.

International Search Report, PCT/US2005/014534, dated Nov. 29, 2005.

International Search Report, PCT/US2006/017981, dated Sep. 7, 2006.

International Search Report, PCT/US2006/028821, dated Mar. 21, 2007.

International Search Report, PCT/US2006/031644, dated Aug. 17, 2007.

International Search Report, PCT/US2006/032811, dated Jan. 25, 2007.

International Search Report, PCT/US2006/033341, dated Aug. 17, 2007.

Seki, Toshihito, et al., "Ultrasonically Guided Percutaneous Microwave Coagulation Therapy for Small Hepatocellular Carcinoma," Cancer, Aug. 1, 1994, vol. 74, No. 3, pp. 817-825.

* cited by examiner

TRIAXIAL ANTENNA FOR MICROWAVE TISSUE ABLATION

CROSS REFERENCE TO RELATED APPLICATION

This application is a continuation of U.S. application Ser. No. 11/452,637 entitled: Microwave Tissue Resection Tool and filed on Jun. 14, 2006, now abandoned which is a continuation in part of U.S. application Ser. No. 10/834,802 entitled: Triaxial Antenna for Microwave Tissue Ablation, filed Apr. 29, 2004 and now issued as U.S. Pat. No. 7,101,369, the disclosures of which are hereby incorporated by reference.

BACKGROUND OF THE INVENTION

The present invention relates to medical instruments for ablating tissue, and in particular to a microwave probe for ablation of tumors and the like.

Microwave ablation (MWA), like radio frequency ablation (RFA), uses localized heating to cause tissue necrosis. However, MWA can produce greater and more rapid heating and can easily support the use of multiple probes because current flow between the probes can be limited. The mode of heating in MWA also eliminates ground pads and charring concerns.

Unfortunately, current MFA equipment produces relatively small lesions because of practical limits in power and treatment time. Power is limited by the current carrying capacity of the small gauge feeder line as it passes through the patient to the site of the necrosis. Larger feeder lines are undesirable because they are not easily inserted percutaneously. Heating of the feeder line at high powers can also lead to burns around the insertion point of the MWA probe.

BRIEF SUMMARY OF THE INVENTION

The present invention provides a triaxial microwave probe design for MWA where the outer conductor allows improved tuning of the antenna to reduce reflected energy through the feeder line. This improved tuning reduces heating of the feeder line allowing more power to be applied to the tissue and/or a smaller feed line to be used. Further, the outer conductor may slide with respect to the inner conductors to permit adjustment of the tuning in vivo to correct for effects of the tissue on the tuning.

Specifically, the present invention provides a probe for microwave ablation having a first conductor and a tubular second conductor coaxially around the first conductor but insulated therefrom. A tubular third conductor is fit coaxially around the first and second conductors. The first conductor may extend beyond the second conductor into tissue when a proximal end of the probe is inserted into a body for microwave ablation. The second conductor may extend beyond the third conductor into the tissue to provide improved tuning of the probe limiting power dissipated in the probe outside of the exposed portions of the first and second conductors.

Thus, it is one object of at least one embodiment of the invention to provide improved tuning of an MWA device to provide greater power to a lesion without risking damage to the feed line or burning of tissue about the feed line and/or to allow smaller feed lines in microwave ablation.

The third tubular conductor may be a needle for insertion into the body. The needle may have a sharpened tip and may use an introducer to help insert it.

Thus, it is another object of at least one embodiment of the invention to provide a MWA probe that may make use of normal needle insertion techniques for placement of the probe.

It is another object of at least one embodiment of the invention to provide a rigid outer conductor that may support a standard coaxial for direct insertion into the body.

The first and second conductors may fit slidably within the third conductor.

It is another object of at least one embodiment of the invention to provide a probe that facilitates tuning of the probe in tissue by sliding the first and second conductors inside of a separate introducer needle.

The probe may include a lock attached to the third conductor to adjustably lock a sliding location of the first and second conductors with respect to the third conductor.

It is thus another object of at least one embodiment of the invention to allow locking of the probe once tuning is complete.

The probe may include a stop attached to the first and second conductors to abut a second stop attached to the third conductor to set an amount the second conductor extends beyond the tubular third conductor into tissue. The stop may be adjustable.

Thus, it is another object of at least one embodiment of the invention to provide a method of rapidly setting the probe that allows for tuning after a coarse setting is obtained.

The second conductor may extend beyond the third conductor by an amount L1 and the first conductor may extend beyond the second conductor by an amount L2 and L1 and L2 may be multiples of a quarter wavelength of a microwave frequency received by the probe.

It is thus another object of at least one embodiment to promote a standing wave at an antenna portion of the probe.

These particular objects and advantages may apply to only some embodiments falling within the claims and thus do not define the scope of the invention.

DETAILED DESCRIPTION OF THE PREFERRED EMBODIMENT

Figure 1:
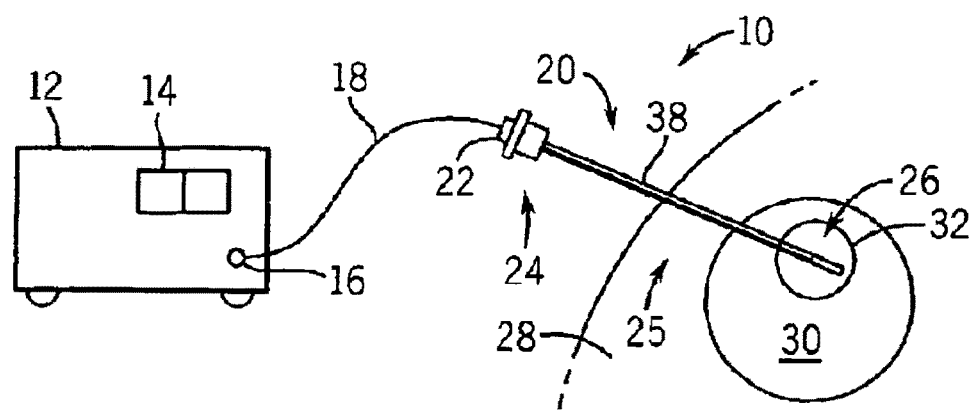
FIG. 1 is a schematic representation of a microwave power supply attached to a probe of the present invention for percutaneous delivery of microwave energy to a necrosis zone within an organ.

Referring now to FIG. 1, a microwave ablation device 10 per the present invention includes a microwave power supply 12 having an output jack 16 connected to a flexible coaxial cable 18 of a type well known in the art. The cable 18 may in turn connect to a probe 20 via a connector 22 at a distal end 24 of the probe 20.

The probe 20 provides a shaft 38 supporting at a proximal end 25 an antenna portion 26 which may be inserted percutaneously into a patient 28 to an ablation site 32 in an organ 30 such as the liver or the like.

The microwave power supply 12 may provide a standing wave or reflected power meter 14 or the like and in the preferred embodiment may provide as much as 100 watts of microwave power of a frequency of 2.45 GHz. Such microwave power supplies are available from a wide variety of commercial sources including as Cober-Muegge, LLC of Norwalk, Conn., USA.

Figure 2:
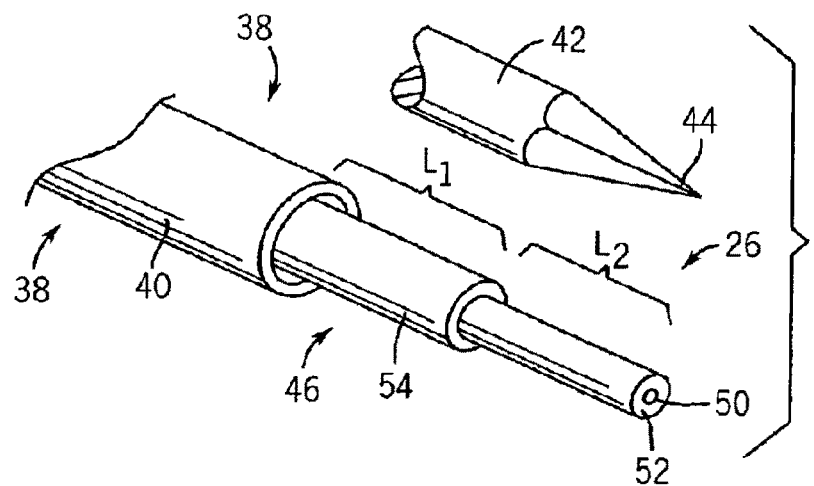
FIG. 2 is a perspective fragmentary view of the proximal end of the probe of FIG. 1 showing exposed portions of a first and second conductor slideably received by a third conductor and showing a sharpened introducer used for placement of the third conductor.

Referring now to FIGS. 1 and 2, generally a shaft 38 of the probe 20 includes an electrically conductive tubular needle 40 being, for example, an 18-gauge needle of suitable length to penetrate the patient 28 to the ablation site 32 maintaining a distal end 24 outside of the patient 28 for manipulation.

Either an introducer 42 or a coaxial conductor 46 may fit within the needle 40. The introducer 42 may be a sharpened rod of a type well known in the art that plugs the opening of the needle 40 and provides a point 44 facilitating the insertion of the probe 20 through tissue to the ablation site 32. The needle 40 and introducer 42 are of rigid material, for example, stainless steel, providing strength and allowing easy imaging using ultrasound or the like.

The coaxial conductor 46 providing a central or first conductor 50 surrounded by an insulating dielectric layer 52 in turn surrounded by a second outer coaxial shield 54. This outer shield 54 may be surrounded by an outer insulating dielectric not shown in FIG. 2 or may be received directly into the needle 40 with only an insulating air gap between the two. The coaxial conductor 46 may, for example, be a low loss 0.86-millimeter coaxial cable.

Referring still to FIG. 2, the central conductor 50 with or without the dielectric layer 52, extends a distance L2 out from the conductor of the shield 54 whereas the shield 54 extends a distance L1 out from the conductor of the needle 40. L1 is adjusted to be an odd multiple of one quarter of the wavelength of the frequency of the microwave energy from the power supply 12. Thus the central conductor 50 in the region of L2 provides a resonant monopole antenna having a peak electrical field at its proximal end and a minimal electric field at the end of the shield 54 as indicated by 56.

At 2.45 GHz, the length L2 could be as little as 4.66 millimeters. Preferably, however, a higher multiple is used, for example, three times the quarter wavelength of the microwave power making L2 approximately fourteen millimeters in length. This length may be further increased by multiple half wavelengths, if needed.

Figure 3:
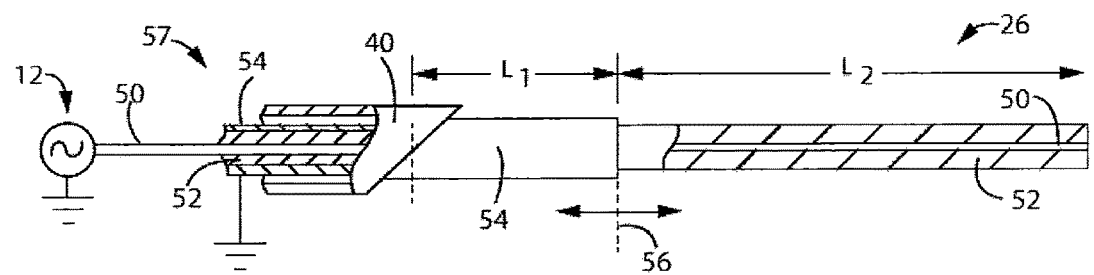
FIG. 3 is a fragmentary cross sectional view of the probe of FIG. 2 showing connection of the microwave power supply to the first and second conductors.

Referring to FIG. 3, the length L1 is also selected to be an odd multiple of one quarter of the wavelength of the frequency of the microwave energy from the power supply 12. When needle 40 has a sharpened or bevel cut tip, distance L1 is the average distance along the axis of the needle 40 of the tip of needle 40.

The purpose of L1 is to enforce a zero electrical field boundary condition at line 56 and to match the feeder line 57 being a continuation of coaxial conductor 46 within the needle 40 to that of the antenna portion 26. This significantly reduces reflected energy from the antenna portion 26 into the feeder line 57 preventing the formation of standing waves which can create hot spots of high current. In the preferred embodiment, L1 equals L2 which is approximately fourteen millimeters.

The inventors have determined that the needle 40 need not be electrically connected to the power supply 12 or to the shield 54 other than by capacitive or inductive coupling. On the other hand, small amounts of ohmic contact between shield 54 and needle 40 may be tolerated.

Figure 4:
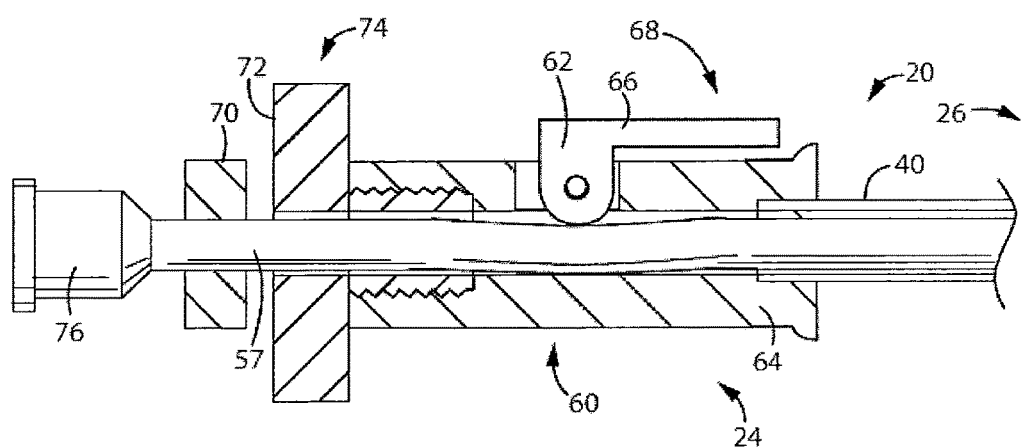
FIG. 4 is a cross sectional view of an alternative embodiment of the probe showing a distal electric connector plus an adjustable stop thumb screw and lock for tuning the probe.

Referring now to FIGS. 1, 2 and 4, during use, the combination of the needle 40 and introducer 42 are inserted into the patient 28, and then the introducer 42 is withdrawn and replaced by a the coaxial conductor 46 so that the distance L2 is roughly established. L2 has been previously empirically for typical tissue by trimming the conductor 50 as necessary.

The distal end 24 of needle 40 may include a tuning mechanism 60 attached to the needle 40 and providing an inner channel 64 aligned with the lumen of the needle 40. The tuning mechanism provides at its distal end, a thumbwheel 72 having a threaded portion received by corresponding threads in a housing of the tuning mechanism and an outer knurled surface 74. A distal face of the thumbwheel provides a stop that may abut a second stop 70 being clamped to the coaxial conductor 46 thread through the tuning mechanism 60 and needle 40. When the stops 70 and on thumbwheel 72 abut each other, the coaxial conductor 46 will be approximately at the right location to provide for extension L1. Rotation of the thumbwheel 72 allows further retraction of the coaxial conductor 46 to bring the probe 20 into tuning by adjusting L1. The tuning may be assessed by observing the reflected power meter 14 of FIG. 1 and tuning for reduced reflected energy.

The tuning mechanism 60 further provides a cam 62 adjacent to the inner channel 64 through which the coaxial conductor 46 may pass so that the cam 62 may press and hold the coaxial conductor 46 against the inner surface of the channel 64 when a cam lever 66 is pressed downwards 68. Thus, once L1 is properly tuned, the coaxial conductor 46 may be locked in position with respect to needle 40.

The distal end of the coaxial conductor 46 may be attached to an electrical connector 76 allowing the cable 18 to be removably attached to disposable probes 20.

The present invention provides as much as a ten-decibel decrease in reflected energy over a simple coaxial monopole in simulation experiments and can create a region of necrosis at the ablation site 32 greater than two centimeters in diameter.

It is specifically intended that the present invention not be limited to the embodiments and illustrations contained herein, but include modified forms of those embodiments including portions of the embodiments and combinations of elements of different embodiments as come within the scope of the following claims.

I claim:

1. A system for microwave ablation for receiving a microwave frequency from a source of microwave electrical power and comprising:
    a probe adapted for insertion into a human tissue, the probe comprising:
      a first conductor;
      a second conductor coaxially surrounding an extent of the first conductor but insulated therefrom, wherein the first and second conductors are adapted to receive electrical conductors communicating with the source of microwave electrical power; and
      a third conductor coaxially surrounding an extent of the second conductor that is coaxially surrounding the extent of the first conductor;
    wherein the first conductor extends beyond the second conductor by a distance of L2;
    wherein the second conductor extends beyond the third conductor by a distance of L1;
    and wherein L1 and L2 are each in length an odd multiple of a quarter wavelength of the microwave frequency conducted through the probe as affected by the human tissue when substantially an entire length of the probe over distance L1 and L2 is in contact with and surrounded by the human tissue and when the microwave frequency conducted through the probe is provided at a frequency of approximately 2.45 Ghz.

2. The system of claim 1, comprising a sharpened tip.

3. The system of claim 1, wherein a portion of the first conductor extending beyond the second conductor is electrically insulated.

4. The system of claim 1, wherein the third conductor has an opening smaller than fourteen gauge.

5. The system of claim 1 including a first connector for transmitting the microwave electrical power from a portion of the electrical conductors communicating with the source of microwave electrical power to a portion of the first conductor outside the human tissue and a second connector for transmitting the microwave electrical power from a portion of the electrical conductors communicating with the source of microwave electrical power to a portion of the second conductor outside the human tissue.

6. The system of claim 5, wherein the electrical conductors communicating with the source of microwave electrical power define a coaxial cable, said probe is removably attachable to the coaxial cable and is disposable.

7. The system of claim 1, wherein the source of microwave electrical power comprises a power supply connected to said first and second connector via a coaxial cable.

8. The system of claim 1, wherein only an insulating air gap is between said second conductor and said third conductor.

9. The system of claim 1, wherein said first conductor terminates at an end of the probe and wherein the distance L1 and distance L2 are selected to provide a peak electrical field at said end.

10. The system of claim 1, wherein the distance L1 and the distance L2 are selected to reduce reflected energy back to the source of microwave power.

11. The system of claim 10, wherein the distance L1 and the distance L2 are of a length to provide a reduction in reflected energy from the first conductor to the second conductor of at least ten decibels relative to a reflected energy from a coaxial monopole, and wherein the electrical conductors communicating with the source of microwave electrical power define a coaxial cable.

12. The system of claim 11, wherein the distance L1 and the distance L2 are selected to permit a region of necrosis at an ablation site of greater than two centimeters in diameter.

13. The system of claim 1, wherein the second and third conductors are adapted for percutaneous insertion into the human tissue.

14. The system of claim 1, wherein a proximal end of the third conductor comprises a sharpened tip.

15. The system of claim 14, wherein the third conductor is formed of a rigid metal.

16. A method of microwave ablation comprising the steps of:
(a) inserting a probe into a human tissue, the probe having a first conductor; a second conductor coaxially surrounding an extent of the first conductor, but insulated therefrom; and a third conductor coaxially surrounding an extent of the second conductor that is coaxially surrounding the extent of the first conductor, wherein the first conductor extends a length L2 from the second conductor and the second conductor extends a length L1 from the third conductor;
(b) supplying the first and second conductors with microwave electrical power from a microwave generator;
(c) tuning the probe by adjusting L1 with respect to L2 to reduce reflected power, wherein L1 and L2 are each in length an odd multiple of a quarter wavelength of a microwave frequency conducted through the probe as affected by the human tissue when substantially an entire length of the probe over distance L1 and L2 is in contact with and surrounded by the human tissue and when the microwave frequency conducted through the probe is provided at a frequency of approximately 2.45 Ghz; and
(d) providing current flow between exposed portions of the first and second conductors ablating the human tissue in a region of the exposed portions of the first and second conductors.

17. A probe for microwave ablation comprising:
a first conductor;
a tubular second conductor coaxially around the first conductor but insulated therefrom; and
a tubular third conductor coaxially around the first and second conductor;
wherein the first conductor extends beyond the second conductor into tissue, when a proximal end of the probe is inserted into a body for microwave ablation, for microwave frequency current flow between the first and second conductors through the tissue;
wherein the second conductor is surrounded by an outer insulating dielectric or an insulating air gap is provided between the second conductor and the third conductor; and wherein
the second conductor extends beyond the third conductor into tissue when an end of the probe is inserted into the body for microwave ablation to provide improved tuning of the probe limiting power dissipated in the probe outside of exposed portions of the first and second conductors; and
the first conductor extends beyond the second conductor by a distance of L2 and the second conductor extends beyond the third conductor by a distance of L1 wherein L1 and L2 are odd multiples of a quarter wavelength of a microwave frequency that the probe is configured to receive.

18. The probe of claim 17 wherein the tubular third conductor is a needle for insertion into the body.

19. The probe of claim 18 wherein the needle has a sharpened tip.

20. The probe of claim 18 including an introducer removably received by the tubular third conductor to assist in penetration of the body by the needle.

21. The probe of claim 17 wherein the third conductor is stainless steel.

22. The probe of claim 17 wherein the first and second conductors fit slidably within the third conductor.

23. The probe of claim 22 further including a lock attached to the third conductor to adjustably lock a sliding location of the first and second conductors with respect to the third conductor.

24. The probe of claim 22 further including a first stop attached to the first and second conductors to about a second stop attached to the third conductor to set an amount the second conductor extends beyond the tubular third conductor into tissue.

25. The probe of claim 24 wherein the first stop is adjustable.

26. The probe of claim 17 wherein the first conductor extends beyond the second conductor by L2 and the second conductor extends beyond the third conductor by L1 wherein L1 equals L2.

27. The probe of claim 17 wherein a portion of the first conductor extending beyond the second conductor is electrically insulated.

28. The probe of claim 17 wherein the third conductor has an opening smaller than 2.108 millimeters (fourteen gauge).

29. The probe of claim 17 including a connector for applying a source of microwave energy to a portion of the probe outside the body.

30. The probe of claim 17, wherein the second conductor extends beyond the third conductor by L1, wherein L1 is selected so as to enforce a zero electrical field boundary condition at a proximal end of the second conductor.

* * * * *